US00PP22801P2

(12) United States Plant Patent
Brown

(10) Patent No.: US PP22,801 P2
(45) Date of Patent: Jun. 19, 2012

(54) ***ANTIRRHINUM* PLANT NAMED 'AACRC03'**

(50) Latin Name: *Antirrhinum majus*
Varietal Denomination: AACRC03

(76) Inventor: Graham Noel Brown, Pennant Hills (AU)

( * ) Notice: Subject to any disclaimer, the term of this patent is extended or adjusted under 35 U.S.C. 154(b) by 0 days.

(21) Appl. No.: 12/802,077

(22) Filed: May 28, 2010

(51) Int. Cl.
*A01H 5/00* (2006.01)

(52) U.S. Cl. ..... Plt./322

(58) Field of Classification Search ..... Plt./322
See application file for complete search history.

*Primary Examiner* — Kent L Bell
(74) *Attorney, Agent, or Firm* — Cassandra Bright

(57) ABSTRACT

A new and distinct *Antirrhinum* cultivar named 'AACRC03' is disclosed, characterized a compact, mounding plant habit, flexible stems and distinctive red/purple flowers. The new variety is an *Antirrhinum,* typically produced as a garden or container plant.

1 Drawing Sheet

Latin name of the genus and species: *Antirrhinum majus.*
Variety denomination: 'AACRC03'.

BACKGROUND OF THE INVENTION

The new cultivar is a product of a planned breeding program. The new variety originated from a cross pollination of the seed parent, an unnamed, unpatented proprietary selection of *Antirrhinum majus* with the pollen parent a different unnamed, unpatented *Antirrhinum majus.* The crossing was made during November of 2005, at a commercial greenhouse in New South Wales Australia. 'AACRC03' was discovered by the inventor, Graham Brown, a citizen of Australia, in New South Wales, at a commercial greenhouse during November of 2007.

Asexual reproduction of the new cultivar 'AACRC03' was first performed in New South Wales, Australia, at a commercial greenhouse by vegetative cuttings in November 2007. 'AACRC03' has since produced several generations and has shown that the unique features of this cultivar are stable and reproduced true to type.

SUMMARY OF THE INVENTION

The cultivar 'AACRC03' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AACRC03.' These characteristics in combination distinguish 'AACRC03' as a new and distinct *Antirrhinum* cultivar:

1. Compact, mounded plant habit.
2. Early flowering.
3. Flexible, non-brittle stems.
4. Distinctive red-purple flowers.

PARENTAL COMPARISON

Plants of the new cultivar 'AACRC03' are similar to the female parent in most horticultural characteristics. However, 'AACRC03' differs in producing a compact, mounding plant, whereas the seed parent has a trailing plant habit. Additionally, the seed parent flowers three weeks later than the new variety.

Plants of the new cultivar 'AACRC03' are similar to the male parent in most horticultural characteristics. However, 'AACRC03' differs in having a compact, mounded plant habit, whereas the pollen has a distinctively upright plant habit.

COMMERCIAL COMPARISON

'AACRC03' can be compared to the commercial variety *Antirrhinum majus* 'Balumrest' U.S. Plant Pat. No. 14,879. Plants of 'Balumdepur' are similar to plants of 'AACRC03' in most horticultural characteristics, however, 'AACRC03' produces a flower with a different color red, and stems that are less brittle.

BRIEF DESCRIPTION OF THE PHOTOGRAPH

The accompanying photograph in FIG. 1 illustrates in full color a typical plant of 'AACRC03' grown outdoors in Lompoc, Calif. This plant is approximately 6 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2001, except where general terms of ordinary dictionary significance are used. The following observations and measurements describe 'AACRC03' plants in a commercial greenhouse in Bodger, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Antrrhinum majus* 'AACRC03'

PROPAGATION

Propagation method: Vegetative Cuttings
Time to initiate roots: About 10 days at 20.degree. C. to 25.degree. C
Time to develop roots: About 20 days at temperatures of 20-25.degree. C.
Root description: Fine, densely fibrous.

PLANT

Growth habit: Mounding annual.
Age of plant described: Approximately 6 months from a rooted cutting.
Container size: 6" pot.
Height: Measured from top soil line of pot, approximately 12 cm.
Plant spread: Approximately 44 cm.
Growth rate: Rapid.
Branching characteristics: Very free branching.
Lateral branches:
*Length.*—Approximately 18 cm.
*Diameter.*—Approximately 0.3 cm.
*Texture.*—Glabrous.
*Color.*—Background Near RHS Yellow-Green 144A.
*Strength.*—Moderate, highly flexible.
*Internode length.*—Approximately 1.1 cm.

FOLIAGE

Leaf:
*Arrangement.*—Simple, opposite. Sessile.
*Average length.*—Approximately 3.0 cm.
*Average width.*—Approximately 0.7 cm.
*Shape of blade.*—Elliptic.
*Apex.*—Acute.
*Base.*—Symmetrical cuneate.
*Margin.*—Entire.
*Texture of top surface.*—Glabrous, matte.
*Texture of bottom surface.*—Glabrous, matte.
*Quantity of leaves per lateral branch.*—Approximately 18.
*Color.*—Young foliage upper side: Near RHS Green 137B. Young foliage under side: Near RHS Green 138C. Mature foliage upper side: Near RHS Green 139A. Mature foliage under side: Near RHS Green 138C. Venation: Type: Pinnate, reticulate. Venation color upper side: Near RHS Yellow-Green 144A. Venation color under side: Near RHS Green 138C.

FLOWER

Natural flowering season: Spring.
Inflorescence description: Single bi-labiate flowers arranged on terminal racemes; flowers facing outward.
Flower longevity on plant: Individual flowers last approximately 1 week.
Quantity of flowers: 3 to 5 per raceme. Approximately 60 open inflorescences per plant.
Inflorescence size:
*Height.*—Approximately 4.5 cm.
*Diameter.*—Approximately 3.5 cm.
Pedicel:
*Length.*—Approximately 0.5 cm.
*Width.*—Approximately 0.1 cm.
*Color.*—Near RHS Yellow-Green 145A.
*Texture.*—Very lightly pubescent.
*Strength.*—Strong.
Flower bud (Just before opening):
*Length.*—Approximately 1.2 cm.
*Diameter.*—Approximately 0.6 cm.
*Shape.*—Ovoid.
*Color.*—Top Near RHS Greyed-Purple 187A, bottom near Yellow-Green N144D.
*Texture.*—Pubescent.
Flowers:
*Flower form.*—Single bi-labiate.
*Flower diameter.*—Approximately 3.2 cm.
*Flower length.*—Approximately 2.8 cm.
*Flower throat diameter.*—Approximately 1.8 cm.
*Flower tube length.*—Approximately 1.4 cm.
Petals:
*Quantity.*—1 upper lip, 2 lobed, 1 lower lip, 3 lobed, with palate.
*Arrangement.*—Lips fused at approximately 50% of length of flower.
*Upper lip, unfused portion.*—Length: Approximately 1.2 cm. Width: Approximately 1.6 cm. Apex: Obtuse. Margin: Entire. Aspect: Strongly curled apex. Texture: Inner side: Glabrous. Outer side: Pubescent. Appearance: Velvety. Color flower tube: At opening: Inner Surface: Near RHS Red-Purple 60A. Outer surface: Near RHS White N155B, with strong flushing near Red-Purple 60A. Mature: Inner Surface: Near RHS Red 53A. Outer surface: Near RHS Red-Purple 59C. Fading: Inner Surface: Near Red-Purple 60B. Outer surface: Near RHS Red-Purple 60C.
*Lower lip, unfused portion.*—Length: Approximately 1.0 cm. Width: Approximately 1.8 cm. Apex: Obtuse. Margin: Entire. Texture: Inner side: Glabrous. Outer side: Pubescent. Appearance: Velvety. At opening: Inner Surface: Near RHS Red-Purple 59B. Outer surface: Near RHS White N155C. Mature: Inner Surface: Near RHS Red 53A. Outer surface: Near RHS Red-Purple 59C. Fading: Inner Surface: Near Purple N79D. Outer surface: Near Red 46C.
Palate:
*Height.*—Approximately 0.8 cm.
*Width.*—Approximately 1.0 cm.
*Texture.*—Glabrous out edge with villous interior. Hairs colored near RHS N155D.
*Appearance.*—Velvety.
*Color.*—At opening: Near RHS Red 53A. Mature: Near RHS Red 53A. Large stripe in center of White N155D. Fading: Near RHS Red 46B.
Sepals:
*Quantity.*—Average 5.
*Appearance.*—Matte.
*Length.*—Approximately 0.8 cm.
*Width.*—Approximately 0.5 cm.
*Shape.*—Ovate.
*Apex.*—Acute.
*Base.*—Obtuse.
*Margin.*—Entire.
*Texture.*—Pubescent.

*Color.*—Inner Surface: Near RHS Green 138A. Outer Surface: Near RHS Green 138A.

Fragrance: Very faint.

REPRODUCTIVE ORGANS

Stamens:

*Number.*—4.

*Filament length.*—Approximately 1.5 cm.

*Filament color.*—Near RHS White N155D.

*Anther length.*—Approximately 1.3 cm.

*Anther color.*—Near RHS Yellow-Orange 15D.

*Anther shape.*—2 lobed ellipse.

*Pollen.*—Moderate.

*Pollen color.*—Near RHS Yellow 9A.

Gynoecium:

Pistil:

*Number.*—1.

*Length.*—Approximately 1.6 cm.

*Style.*—Length: Approximately 1.1 cm. Color: Near RHS Red-Purple 60A.

*Stigma.*—Shape: Globular. Color: Near RHS Yellow-Green 145A. Ovary color: Near RHS Yellow-Green 145C.

OTHER CHARACTERISTICS

Seeds and fruits: Not observed to date.

Disease/pest resistance: Neither resistance nor susceptibility to normal diseases and pests of *Antirrhinum* has been observed.

Temperature tolerance: Tolerates temperatures from approximately −1° C. to 32° C.

Drought tolerance: No tolerance for drought.

What is claimed is:

1. A new and distinct cultivar of *Antirrhinum* plant named 'AACRC03' as herein illustrated and described.

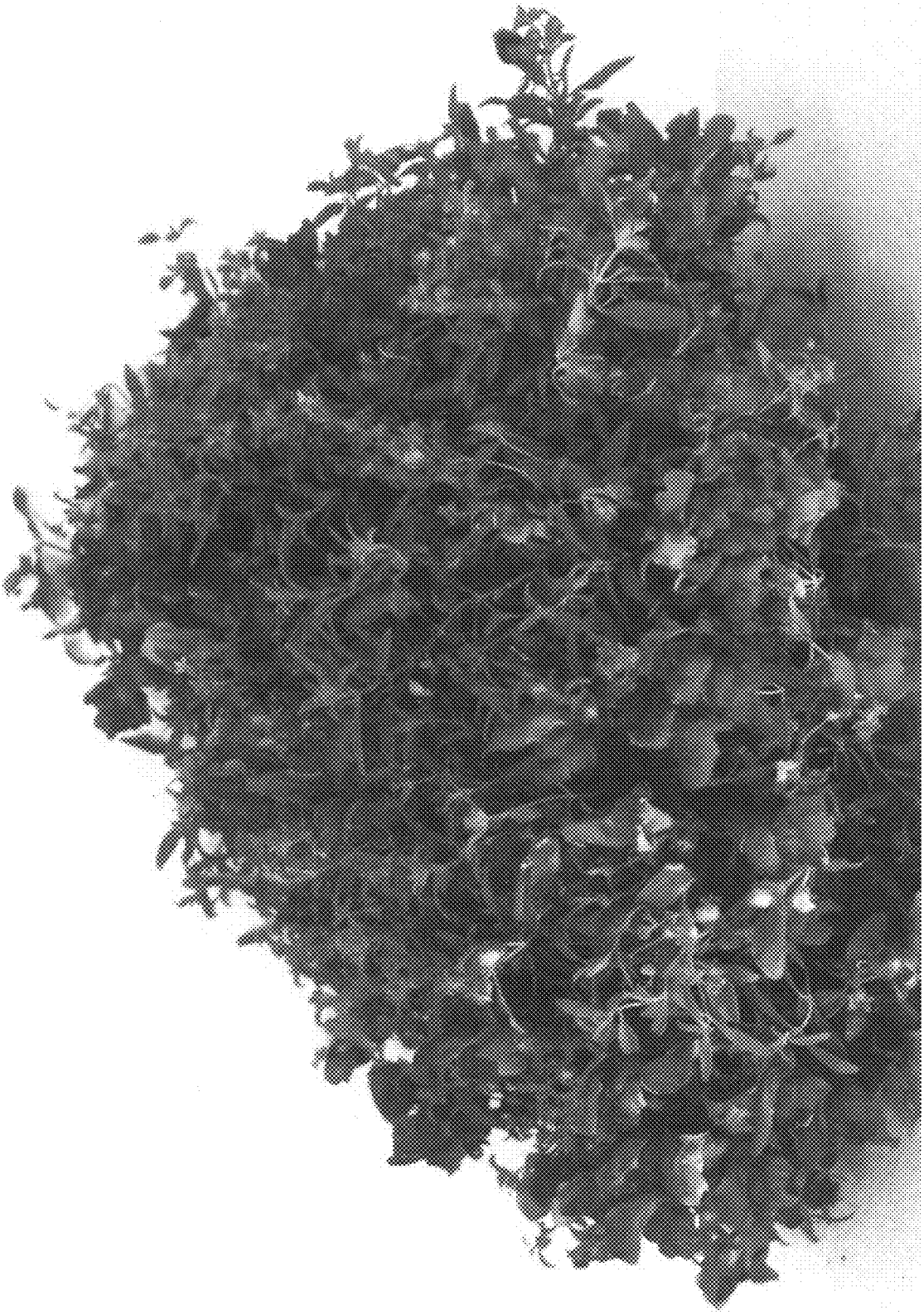

* * * * *